US011944372B2

(12) United States Patent
Cao et al.

(10) Patent No.: US 11,944,372 B2
(45) Date of Patent: Apr. 2, 2024

(54) ABLATION PROBE SYSTEM WITH CENTER WORKING CHANNEL

(71) Applicant: Boston Scientific Scimed, Inc., Maple Grove, MN (US)

(72) Inventors: Hong Cao, Maple Grove, MN (US); Larry D. Canady, Jr., Ham Lake, MN (US); Timothy A. Ostroot, Cokato, MN (US); Bruce R. Forsyth, Hanover, MN (US); Jonathan Tyler Gorzycki, Blaine, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 322 days.

(21) Appl. No.: 16/659,111

(22) Filed: Oct. 21, 2019

(65) Prior Publication Data

US 2020/0155227 A1 May 21, 2020

Related U.S. Application Data

(60) Provisional application No. 62/749,337, filed on Oct. 23, 2018.

(51) Int. Cl.
*A61B 18/14* (2006.01)
*A61B 8/12* (2006.01)
(Continued)

(52) U.S. Cl.
CPC ............ *A61B 18/1492* (2013.01); *A61B 8/12* (2013.01); *A61B 18/1477* (2013.01);
(Continued)

(58) Field of Classification Search
CPC .................. A61B 18/1492; A61B 8/12; A61B 2018/0016; A61B 2018/00214;
(Continued)

(56) References Cited

U.S. PATENT DOCUMENTS

| 5,672,173 A | 9/1997 | Gough et al. |
| 5,740,808 A * | 4/1998 | Panescu ............... A61B 5/6853 600/585 |

(Continued)

FOREIGN PATENT DOCUMENTS

| CN | 112888391 | 6/2021 |
| WO | 2006073879 | 7/2006 |
| WO | 2020086588 | 4/2020 |

OTHER PUBLICATIONS

"International Preliminary Report on Patentability," for PCT Application No. PCT/US2019/057447 dated May 6, 2021 (9 pages).
(Continued)

*Primary Examiner* — Sean W Collins
(74) *Attorney, Agent, or Firm* — Pauly, DeVries Smith & Deffner LLC

(57) ABSTRACT

One general aspect includes a system for ablation including a catheter including a sheath defining a sheath lumen and a distal end, and an elongate electrode assembly axially moveable within the sheath lumen. The electrode assembly includes a shaft defining a central channel and a distal central channel opening. The electrode assembly also includes an expandable electrode array including two or more electrode elements positioned at the distal portion of the electrode assembly, where the electrode array is moveable between a retracted position contained within the sheath lumen and an expanded position protruding from the sheath.

14 Claims, 5 Drawing Sheets

(51) Int. Cl.
*A61B 10/02* (2006.01)
*A61B 18/00* (2006.01)
*A61B 18/18* (2006.01)

(52) U.S. Cl.
CPC ...... *A61B 18/1482* (2013.01); *A61B 10/0233* (2013.01); *A61B 2018/0016* (2013.01); *A61B 2018/00214* (2013.01); *A61B 2018/00577* (2013.01); *A61B 2018/00613* (2013.01); *A61B 2018/00636* (2013.01); *A61B 2018/143* (2013.01); *A61B 2018/1432* (2013.01); *A61B 2018/1475* (2013.01); *A61B 2018/1823* (2013.01); *A61B 2018/1861* (2013.01)

(58) Field of Classification Search
CPC ........... A61B 2018/00577; A61B 2018/00613; A61B 2018/00636; A61B 2018/1475; A61B 2018/1823; A61B 2018/1861
See application file for complete search history.

(56) References Cited

U.S. PATENT DOCUMENTS

| | | | |
|---|---|---|---|
| 5,957,849 A * | 9/1999 | Munro | A61B 18/149 600/463 |
| 7,517,346 B2 | 4/2009 | Sloan et al. | |
| 8,206,308 B2 | 6/2012 | Marshall et al. | |
| 8,257,267 B2 | 9/2012 | Thornton | |
| 8,414,580 B2 | 4/2013 | Rioux et al. | |
| 8,414,581 B2 | 4/2013 | Shah et al. | |
| 9,451,929 B2 | 9/2016 | Sadaka | |
| 9,770,290 B2 * | 9/2017 | Young | A61B 18/148 |
| 9,955,946 B2 | 5/2018 | Miller et al. | |
| 2003/0093007 A1 | 5/2003 | Wood et al. | |
| 2011/0071400 A1 | 3/2011 | Hastings et al. | |
| 2012/0220994 A1 | 8/2012 | Pearson et al. | |
| 2012/0253197 A1 | 10/2012 | Sadaka | |
| 2013/0190756 A1 | 7/2013 | Rioux et al. | |
| 2014/0336639 A1 * | 11/2014 | Young | A61B 18/148 606/41 |
| 2015/0011834 A1 * | 1/2015 | Ayala | A61B 17/0218 29/428 |
| 2016/0000313 A1 | 1/2016 | Mesallum | |
| 2016/0008053 A1 | 1/2016 | Mathur et al. | |
| 2017/0007310 A1 * | 1/2017 | Rajagopalan | A61B 18/1815 |
| 2017/0105793 A1 | 4/2017 | Cao et al. | |
| 2020/0367965 A1 * | 11/2020 | Hancock | A61B 18/1492 |

OTHER PUBLICATIONS

"International Search Report and Written Opinion," for PCT Application No. PCT/US2019/057447 dated Jan. 20, 2020 (14 pages).
"Response to Communication Pursuant to Rules 161 and 162 EPC," for European Patent Application No. 19802396.2 filed Nov. 12, 2021 (11 pages).

* cited by examiner

ABLATION PROBE SYSTEM WITH CENTER WORKING CHANNEL

This application claims the benefit of U.S. Provisional Application No. 62/749,337 filed Oct. 23, 2018, the content of which is herein incorporated by reference in its entirety.

BACKGROUND

Radiofrequency ablation (RF ablation) uses thermal energy to heat abnormal tissue, causing cell death. As the tissue is heated, the temperature of the tissue increases. Additionally, the change in the tissue caused by the heating changes the impedance of the tissue. Radiofrequency ablation treatments can be monitored using temperature, impedance, and external imaging such as a computed tomography (CT) imaging or external ultrasound imaging.

Reversible and irreversible electroporation are non-thermal treatments that use pulsed electrical energy to create pores in tissue cell walls. After reversible electroporation, the cells are able to be healed through normal biological processes. Irreversible electroporation creates pores in the cell that damage the cell walls such that the cells cannot be healed, leading to cell death through late stage apoptosis.

SUMMARY

One general aspect includes a system for ablation including a catheter including: a sheath defining a sheath lumen and a distal end, an elongate electrode assembly within the sheath lumen, the electrode assembly having a distal portion and a proximal portion, the electrode assembly being axially moveable within the sheath lumen. The electrode assembly includes a shaft defining a central channel and a distal central channel opening. The electrode assembly also includes a first lead within the shaft. The electrode assembly also includes an expandable electrode array including two or more electrode elements positioned at the distal portion of the electrode assembly and electrically connected to the first lead, where the electrode array is moveable between a retracted position contained within the sheath lumen and an expanded position protruding from the sheath, where the electrode elements surround the distal central channel opening of the shaft when the electrode elements are in the expanded position.

Implementations may include one or more of the following features. The system where the electrode elements protrude from a distal end of the sheath in the expanded position. The system where the electrode elements include electrode tines, where the electrode tines are moved to the expanded position when a linear force is applied to the electrode assembly within the sheath lumen so that the electrode assembly protrudes from the distal end of the sheath. The system where a position of the electrode tines in the expanded position is adjustable by adjusting an amount of protrusion of the electrode tines from the distal end of the sheath. The system where the shaft defines an inner surface and the first lead is positioned on the inner surface. The system where the shaft is a tube including a solid wall. The system further including an ancillary device configured to be introduced into and slidably moved within the central channel. The system where the ancillary device is capable of being moved axially to a first deployed position extending from the distal central channel opening. The system where the ancillary device can be moved axially between the first deployed position and a second deployed position, where the ancillary device extends away from the central channel opening by a first distance in the first deployed position and by a different second distance in the second deployed position. The system where the ancillary device is selected from a group including of: a sensor, an ultrasound imaging catheter, a biopsy needle, a drug delivery device, a liquid delivery device, an accelerometer, a force sensor, a temperature sensor, a thermal camera, and an optical camera. The system where the ancillary device includes an ultrasound imaging catheter and where the system further includes a computer processor in communication with the ultrasound imaging catheter, where the processor is configured to generate an image of tissue capable of showing a change in tissue due to ablation. The system where the ancillary device includes a sensor and where the system further includes a processor in communication with the sensor, where the processor is configured to generate at least one of the group including of a signal corresponding to an impedance of tissue to detect a change in tissue due to ablation and a signal corresponding to a temperature of tissue to detect a change in tissue due to ablation. The system where the electrode assembly is configured for fluid delivery through the central channel. The system further including a generator configured to be electrically connected to the electrode assembly and for delivery of one of the group including of a radiofrequency energy, a pulsed electric field, an irreversible electroporation energy, and a reversible electroporation energy.

One general aspect includes a system for ablation including a catheter including: a sheath defining a sheath lumen and a distal end, an elongate electrode assembly within the sheath lumen, the electrode assembly having a distal portion and a proximal portion, the electrode assembly being axially moveable within the sheath lumen. The electrode assembly also includes a shaft defining a central channel and a distal central channel opening. The electrode assembly also includes a first lead within the shaft. The electrode assembly also includes an expandable electrode array including three or more electrode elements positioned at the distal portion of the electrode assembly and electrically connected to the first lead, where the electrode array is moveable between a retracted position contained within the sheath lumen and an expanded position protruding from a distal end of the sheath, where the electrode elements surround the distal central channel opening of the shaft when the electrode elements are in the expanded position. The system also includes an ultrasound imaging catheter configured to be introduced into and slidably moved within the central channel, where the ultrasound imaging catheter is capable of being moved axially to a first deployed position extending from the distal central channel opening. The system also includes a generator configured to be electrically connected to the electrode assembly and configured for delivery of one of the group including of a radiofrequency energy, a pulsed electric field, an irreversible electroporation energy, and a reversible electroporation energy.

Implementations may include one or more of the following features. The system where the electrode elements include electrode tines, where the electrode tines are moved to the expanded position when a linear force is applied to the electrode assembly within the sheath lumen so that the electrode assembly protrudes from the distal end of the sheath.

One general aspect includes an ablation method including providing an ablation probe having a sheath having a sheath lumen, an electrode assembly defining a central channel and including an expandable electrode array including two or more electrode elements positioned at a distal portion of the electrode assembly, where the electrode array is moveable between a retracted position contained within the sheath lumen and an expanded position protruding from the sheath, where the electrode elements surround a distal central channel opening when the electrode elements are in the expanded position, and an ancillary device configured to be inserted in the central channel. The ablation method also includes inserting the sheath into tissue of a patient. The ablation method also includes inserting the electrode assembly into the sheath lumen. The ablation method also includes while the electrode assembly is inside of the sheath lumen, ablating the tissue using the electrode assembly. The ablation method also includes while the electrode assembly is inside of the sheath lumen, inserting the ancillary device into the central channel of the electrode assembly.

Implementations may include one or more of the following features. The ablation method further including, after the step of inserting the electrode assembly into the sheath lumen, expanding the electrode elements into the patient tissue; and performing the step of ablating the tissue after the electrode elements have been expanded. The ablation method further including, while the ancillary device is inside of the electrode assembly, using the ancillary device to perform at least one of the following steps: capturing an image of the patient tissue, sensing a condition of the patient tissue, delivering a fluid into the patient tissue, or removing at least a portion of the patient tissue through the central channel. The ablation method where the ancillary device is an ultrasound imaging catheter and the tissue is ablated using irreversible electroporation, the method further including the steps of: inserting the ultrasound imaging catheter into a proximal end of the central channel and out a distal end of the central channel such that the ultrasound imaging catheter protrudes from the distal portion of the electrode assembly; and capturing an ultrasound image of the patient tissue while the ultrasound imaging catheter protrudes from the distal portion of the electrode assembly.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

DETAILED DESCRIPTION

Figure 1:
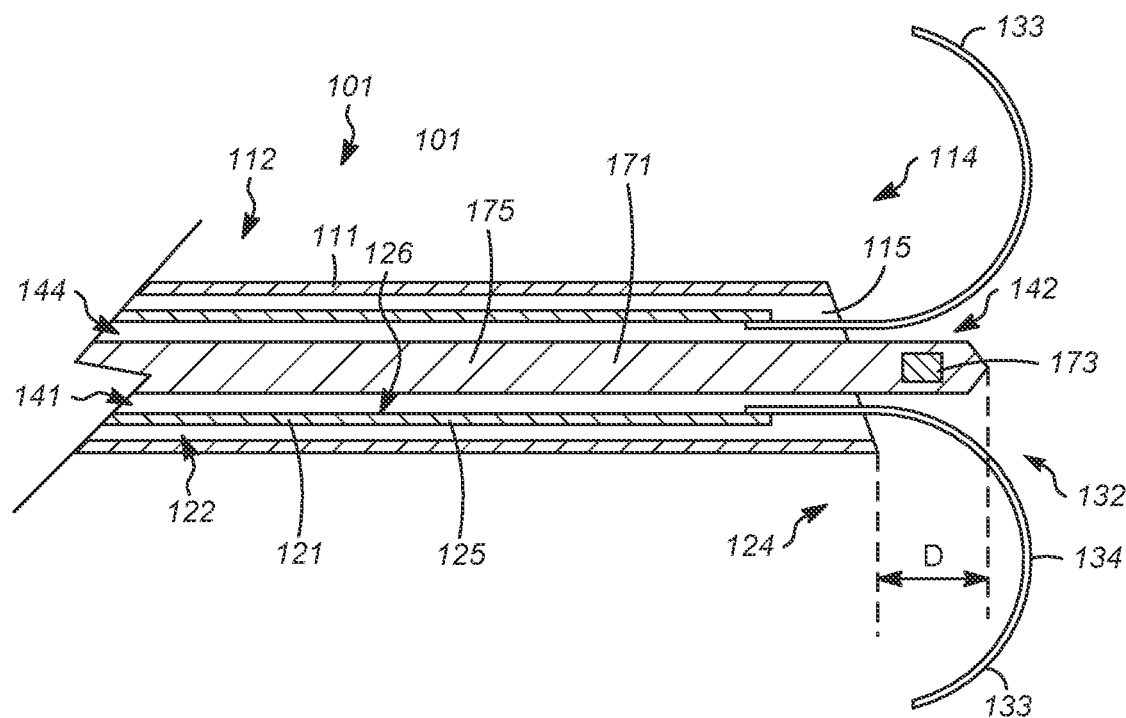
FIG. 1 is a cross-sectional view of an ablation catheter with a center working channel according to some examples.

The present disclosure provides an ablation system that combines a sheath and an elongate electrode assembly within a lumen of the sheath. The elongate electrode assembly defines a central channel, which will also be referred to as a central working channel or working channel. In some embodiments, the central channel is centered within the elongate electrode assembly. In some embodiments, the central channel is not centered. One or more ancillary devices are configured to be inserted into the central channel of the electrode assembly to monitor or assist an ablation treatment.

The ablation system described here can be implemented with a number of different types of ablation, including radiofrequency ablation (RF ablation) and pulsed electric field (PEF) treatment, which includes reversible electroporation and irreversible electroporation (IRE). The ablation system includes an ablation probe, also referred to as an ablation catheter.

Irreversible electroporation leads to cell death without substantially heating the tissue to be ablated. Therefore, measuring the temperature of the tissue being ablated does not provide detailed information related to the progress of the ablation treatment. Tissue impedance does change during the treatment, however, and therefore impedance measurements may provide information related to the progress of the treatment.

The central working channel of the elongate electrode assembly is used to introduce one or more ancillary devices into the patient's body. In some examples, the ancillary devices can be used to monitor the progress of an ablation treatment. In some examples, the ancillary devices can be used to aid in the ablation treatment. The configuration provided by the ablation probe of the current disclosure allows such monitoring and treatment directly at the ablation site. The ancillary devices can move axially within the probe. As used herein, axial motion refers to movement of a device through a center lumen from a proximal location in the lumen to a distal location in the lumen, along the axis of the lumen. As used herein, the words proximal and distal express a spatial relationship between two portions. A portion that is designated as being distal is positioned closer to the insertion end of the system than a portion that is designated as being proximal.

In some examples, the ancillary devices can be introduced sequentially. For example, a first ancillary device is introduced into the central channel of the electrode assembly, then the first ancillary device is removed from the central channel of the electrode assembly, and then a second ancillary device is introduced into the central channel. In some examples, the second ancillary device is introduced into the central channel without removing of the first ancillary device.

In some examples, the ancillary devices can be introduced simultaneously. For example, the first ancillary device and second ancillary device are introduced into the central channel of the electrode assembly. In some examples, more than one ancillary device or function can be combined as a single device.

The electrode assembly can include electrode tines or other extendable electrodes that can be moved from the inside of the sheath lumen to the outside of the sheath lumen and into patient tissue. The electrodes can be deployed before an ancillary device is introduced into the central channel, or while the ancillary device is within the central channel, or after the ancillary device has been removed from the central channel. In other words, the electrodes are movable and deployable independently of the axial movement of the ancillary devices. The electrode assembly is axially movable within the sheath lumen independently of the axial movement of the ancillary devices.

The ablation system can include multiple ancillary devices each having different features. The modularity provided by the ablation probe of the current disclosure allows different ancillary devices to be positioned within the body of the patient while ablation electrodes are deployed in the patient tissue, without having to change the position of the deployed electrodes or the position of the probe. In addition, the ancillary devices can be used to determine whether the probe and deployed electrodes are correctly placed in the patient tissue, and this information can be used to adjust the position of the probe or the electrodes.

For example, one or more ancillary devices can be used for in situ visualization of lesion formation in tissue to be ablated. This includes, for example, an ultrasound imaging catheter capable of capturing a two-dimensional (2D) or three-dimensional (3D) ultrasound image of the tissue being ablated. This can also include imaging using electromagnetic waves, such as a camera that senses electromagnetic waves in the visual or infrared (thermal) wavelength spectrum.

The ancillary devices can include sensor probes. For example, a temperature sensor or impedance sensor can be included. The ancillary devices can also include biopsy needles for tissue biopsy, and liquid injection devices that can introduce liquids into the patient tissue in connection with treatment of the tissue or to assist the ablation.

In some examples, the ancillary devices are capable of being extended out of the distal tip of the probe shaft, extending past the end of the distal tip and into the patient tissue.

The examples provided herein can ensure that a target tumor is destroyed with a sufficient ablation margin, and enables physicians to reduce the likelihood of damage to surrounding healthy tissue, critical organs, and major blood vessels. Additionally, the location of the ancillary device allows for monitoring near the center of the ablation lesion, and nearer to the far edge of the ablated region opposite from the ablation probe. An ancillary device, such as an ultrasound catheter, can monitor the lesion shape and look for bubble formation due to heat, tissue dehydration due to heat, or tissue edema due to fluid ingress. One application example is ablation of liver lesions.

Examples of an Ablation Catheter

Turning now to the drawings, FIG. 1 is a cross-sectional view of an ablation catheter with a center working channel according to some examples. The ablation catheter 101 includes a sheath 111 and an elongate electrode assembly 121. The sheath 111 has a proximal end 112 and a distal end 114. The sheath 111 defines a sheath lumen 115.

The sheath 111 can be made of metals such as stainless steel or polymers such as PEBAX™ available from Arkema, which has a location at King of Prussia, Pennsylvania, USA, using machining or extrusion. The sheath 111 can have an inner diameter of 0.01 inches (25 Ga, 0.25 mm) to 0.106 inches (10 Ga, 2.69 mm), likely 0.016 inches (22 Ga, 0.41 mm) to 0.085 inches (12 Ga, 2.16 mm) and preferably 0.042 inches (17 Ga, 1.07 mm) to 0.063 inches (14Ga, 1.60 mm).

The sheath 111 can have an outer diameter of 0.02 inches (25 Ga, 0.51 mm) to 0.134 inches (10 Ga, 3.40 mm), likely 0.028 inches (22 Ga, 0.71 mm) to 0.0109 inches (12 Ga, 0.28 mm) and preferably 0.058 inches (17 Ga, 1.47 mm) to 0.083 inches (14 Ga, 2.11 mm). The sheath 111 can comprise a solid wall having a thickness of between 0.005 inches (0.127 mm) and 0.05 inches (1.27 mm). The sheath 111 can have a length of between 5 centimeters and 30 centimeters.

In some examples, the sheath 111 can be made of a metal including stainless steel. In some examples, the sheath 111 is a stainless steel cannula with an inner diameter of about 0.075 inch (1.9 mm), a wall thickness of about 0.025 inch (0.64 mm), and a sharp trocar tip. Many other dimensions are possible for the sheath. In some examples, the sheath 111 includes an insulation layer to insulate it from the elongate electrode assembly 121. The insulation layer can be a polyimide insulation layer, which, in some examples, has an inner diameter of about 0.068 inch (1.7 mm) and a wall thickness of about 0.025 inch (0.64 mm). Alternatively or in addition, the insulation layer can include insulators such as polyethylene terephthalate (PET), polyether ether ketone (PEEK), polytetrafluoroethylene (PTFE) (or other fluoropolymers), fluorinated ethylene propylene (FEP), or combinations of these materials.

The electrode assembly 121 includes a shaft 125 and is configured to be positioned within the sheath lumen 115. The electrode assembly 121 is axially movable within the sheath lumen 115. The electrode assembly 121 has a distal portion 124 and a proximal portion 122. At the distal portion 124 of the electrode assembly 121 is an expandable electrode array 132. The electrode array 132 is configured for tissue ablation, which can include one or more of radiofrequency ablation, pulsed electric field ablation, reversible electroporation, and irreversible electroporation. The electrode array 132 has electrode elements 133, which in the example of FIG. 1 comprise multiple tines 134. The electrode array 132 is electrically coupled to an external source of ablation energy by a lead within the shaft 125. In some examples, the shaft 125 defines an inner surface 126, and the lead is positioned on the inner surface 126.

In the example of FIG. 1, the tines 134 are attached to an inner surface 126 of the shaft 125. In some examples, the tines 134 are made of electrical conductive alloy material such as stainless steel (SS). In some examples, the tines 134 are made of a shape memory alloy material such as nickel titanium alloy (nitinol).

The shaft 125 defines a central channel 141 in the electrode assembly 121. In some examples, the shaft 125 is a tube comprising a solid wall, and the interior lumen of the tube comprises the central channel 141. The central channel 141 has a distal central channel opening 142 and a proximal central channel portion 144. The central channel 141 is configured to receive an ancillary device 175 that can be introduced into and slidably moved within the central channel 141. In one example implementation, the central channel 141 has a diameter of about 0.0295 inch (0.75 mm). In one example implementation, the central channel 141 has a diameter of about 0.027 inch (0.69 mm).

An ancillary device 175 is configured to be slidably movable within the central channel 141. The ancillary device 175 can have one of a number of different features, such as sensing, monitoring, imaging, biopsy, or liquid delivery. Some options for individual ancillary devices 175 are provided and described more fully below with respect to FIGS. 7-10. The ancillary device 175 is sized to fit inside of the central channel 141. In one example implementation, the ancillary device 175 has an outer diameter of less than about 0.027 inch (0.69 mm). In one example implementation, the ancillary device 175 has an outer diameter of less than about 0.0295 inch (0.75 mm).

In the example of FIG. 1, the ancillary device 175 is an ultrasound imaging catheter 171. The ultrasound imaging catheter 171 includes an ultrasound transducer 173 that is configured for ultrasound imaging of patient tissue. The ancillary device 175 can be deployed into patient tissue for monitoring or therapy. When the ancillary device 175 is retracted fully inside of the central channel 141, it is designated as being in a retracted configuration. When the ancillary device 175 is slidably moved such that it protrudes out of the distal end 114 of the sheath 111, it is designated as being in a deployed configuration. FIG. 1 shows the ancillary device 175 in a deployed position in which the distal tip 176 of the ancillary device 175 protrudes beyond the distal end 114 of the sheath 111. During an ablation procedure, when the ancillary device 175 is in a deployed position, the ancillary device 175 is in or near tissue to be ablated. As can be seen in FIG. 1, the ancillary device 175 extends away from the central channel opening 142 by a distance D. Increasing or decreasing the distance D changes the deployed position of the ancillary device.

Figure 2:
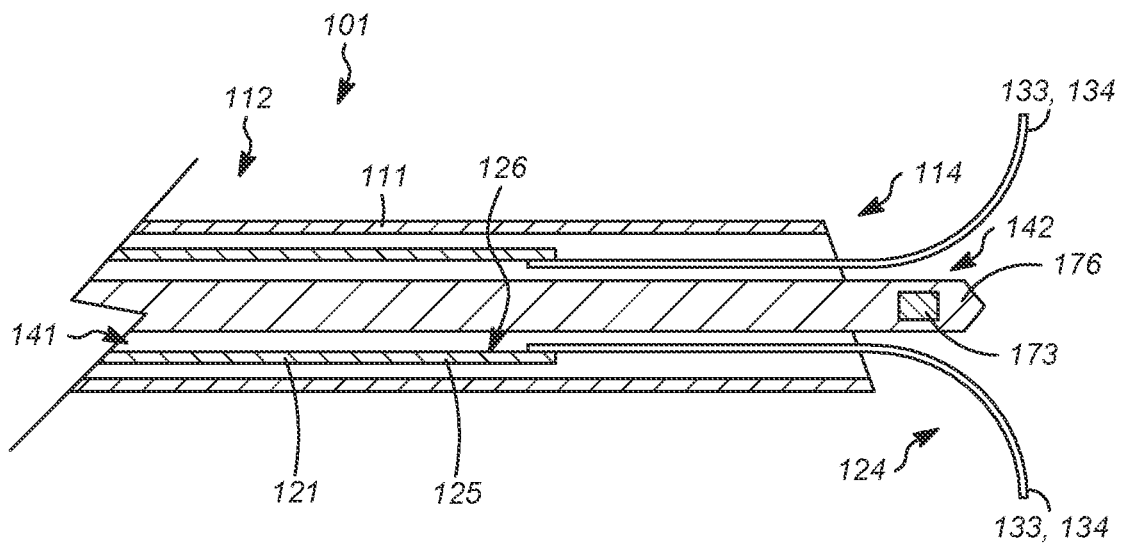
FIG. 2 is a cross-sectional view of the ablation catheter of FIG. 1 with tines partially retracted.
Figure 3:
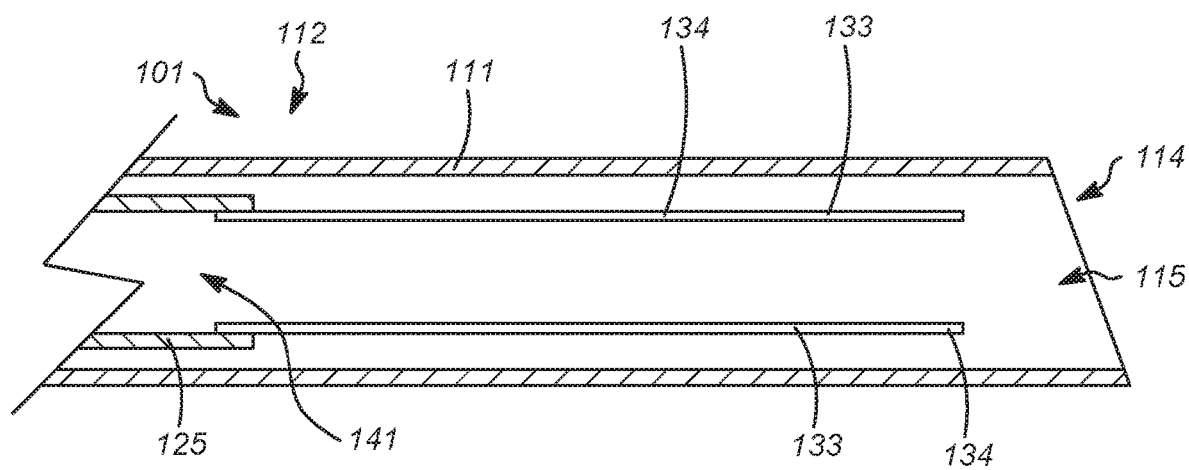
FIG. 3 is a cross-sectional view of the ablation catheter of FIG. 1 with the tines retracted inside the probe.

Referring now to FIGS. 1-3, in some examples, the electrode assembly 121 has an expanded configuration and a retracted configuration. FIG. 2 is a cross-sectional view of the ablation probe of FIG. 1 with tines partially retracted, and FIG. 3 is a cross-sectional view of the ablation probe of FIG. 1 with the tines retracted inside the probe. The electrode assembly 121 is axially moveable within the sheath lumen 115 to cause the electrode elements 133 to deploy or retract. In the examples of FIGS. 1-3, the electrode tines 134 are moved from the retracted position shown in FIG. 3 to the expanded position shown in FIG. 1 when a linear force is applied to the electrode assembly 121, as when the electrode assembly 121 is moved axially within the sheath lumen 115. Applying the linear force urges the tines 134 out of the distal end 114 of the sheath. In this configuration, the electrode assembly 121 protrudes from the distal end 114 of the sheath 111. The position of the electrode tines 134 in patient tissue can be adjusted by changing the amount of protrusion of the electrode tines 134 from the distal end 114 of the sheath 111. For example, FIG. 2 shows the electrode array 132 in a partially expanded state. Applying a force to the shaft 125 in the direction of the distal end 114 of the sheath 111 changes the expanded position of the tines 134 so that the electrode tines 134 extend further from the distal end 114 of the sheath 111, as in FIG. 1.

Figure 4:
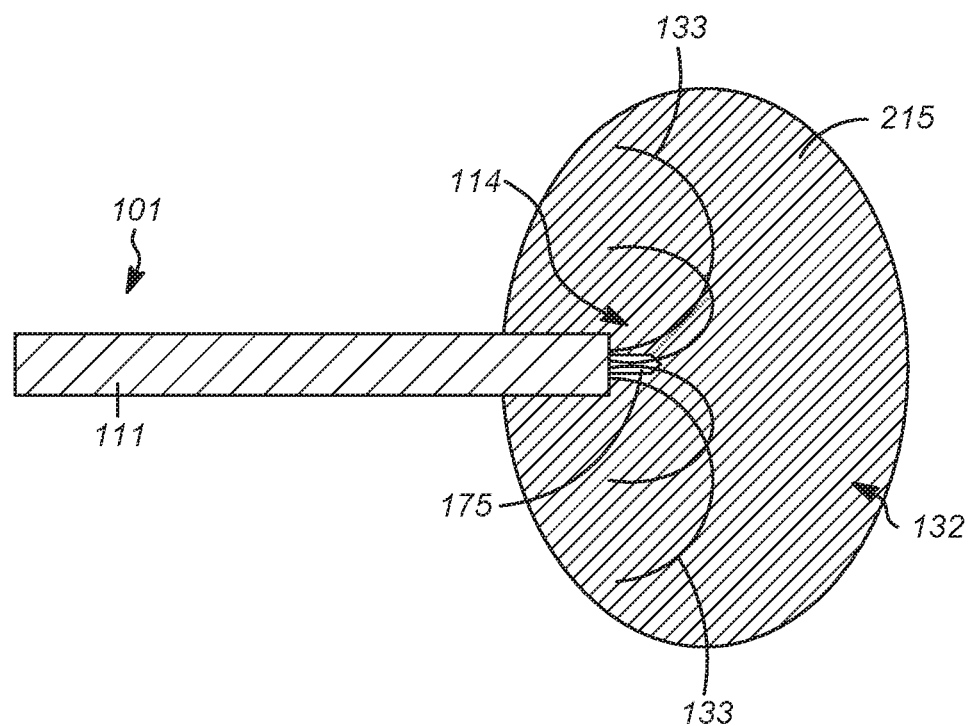
FIG. 4 is a schematic side view of the ablation catheter of FIG. 1 inserted in a tumor according to some examples.

FIG. 4 is a schematic view of an ablation catheter inserted in a tumor according to some examples. The examples provided in the present disclosure can ensure that a target tumor is destroyed with a sufficient ablation margin, and enables physicians to avoid damage to surrounding healthy tissue, critical organs, and major blood vessels. Additionally, the location of the ancillary device allows for monitoring near the center of the ablation lesion, and nearer to the far edge of the ablated region opposite from the ablation probe. FIG. 4 shows the ablation catheter 101 having multiple electrode elements 133 deployed within tissue to form a lesion 215 via ablation. An ancillary device 175 protrudes into the lesion 215. The ancillary device 175 can be moved axially to protrude further into the lesion 215 or to retract further toward the distal end 114 of the sheath 111.

Compared to a straight needle ablation probe, an ablation catheter with an expandable electrode array can be used to create a lesion where a smaller portion of the lesion overlaps with the shaft. The expandable electrodes can help to create a lesion with a larger dimension extending radially away from a longitudinal axis of the shaft.

Figure 5:
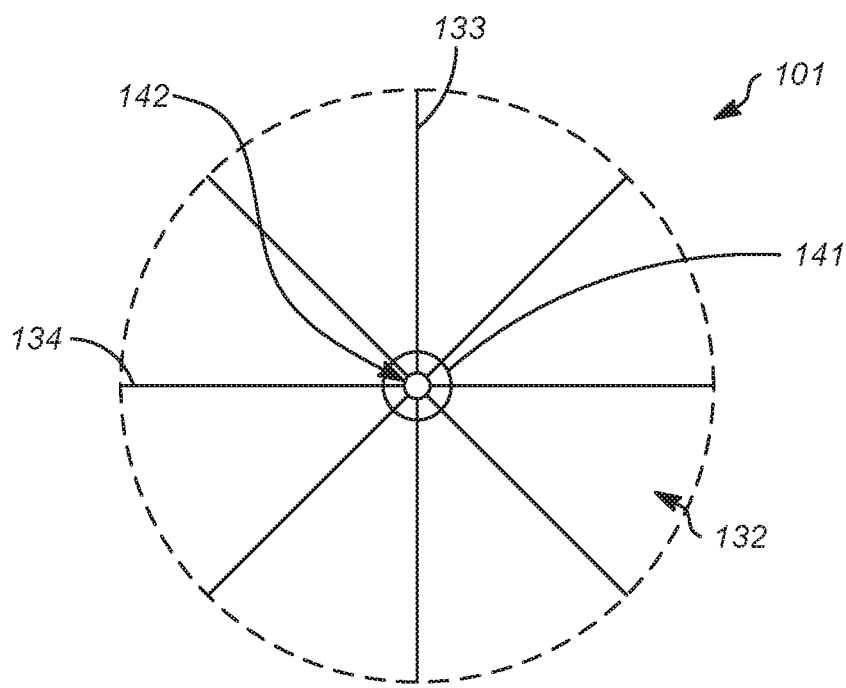
FIG. 5 is a schematic end view of the ablation catheter of FIG. 1 according to some examples.

FIG. 5 is a schematic end view of an ablation catheter 101 according to some examples, where the viewer is looking down a longitudinal axis of the ablation catheter. In the view of FIG. 5, the distal central channel opening 142 of the central channel 141 can be seen. The electrode array 132 is shown in an expanded position, with the electrode tines 134 creating an umbrella-like structure. In the example of FIG. 5, the electrode elements 133 are approximately evenly spaced around the outer region of the ablation catheter 101. The electrode elements 133 of the electrode array 132 surround the distal central channel opening 142 of the shaft 125, such that the opening 142 is approximately centered in an imaginary circle created by the outer edges of the electrode tines 134. This in turn allows an ancillary device inserted into the central channel 141 to be surrounded by the electrode elements 133 when the device protrudes from the distal end 114 of the sheath 111. This enables improved monitoring of the ablation procedure and improved supplemental treatment (such as drug delivery to the tissue) because the ancillary device is centrally located in the region of the ablation lesion. In addition or alternatively, the electrode elements 133 of the electrode array 132 surround the central channel 141 of the shaft 125, such that the central channel 141 is approximately centered in an imaginary circle created by the outer edges of the electrode tines 134.

Figure 6:
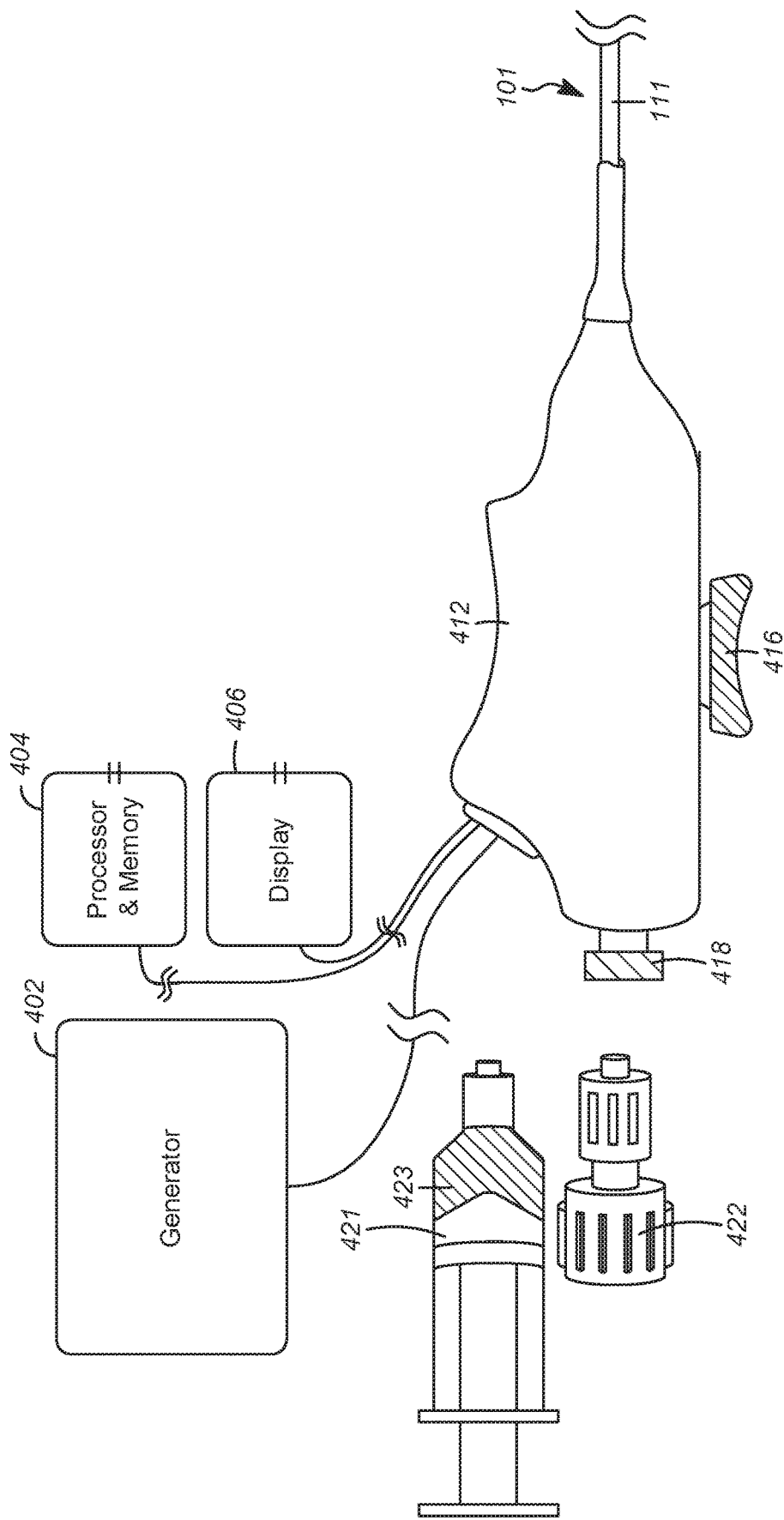
FIG. 6 is a schematic view of an ablation system according to some examples.

FIG. 6 is a schematic view of an ablation system according to some examples. The system includes a generator 402 capable of generating ablation energy, a computer processor 404, and a display 406. The ablation catheter 101 is operably connected to a handle assembly 412, which includes an actuator 416 for deploying and retracting the electrode assembly (not shown). The actuator 416 is operably connected to the electrode assembly to slidably move the electrode assembly in relation to the sheath 111.

A port 418 is provided in the handle assembly 412 for introducing one or more ancillary devices into the central channel. In some examples, the port 418 can be a female Luer lock capable of interconnecting with one of a number of different devices. For example, the port 418 can receive a valve 422 or a syringe 421 containing a deliverable 423. The port 418 can receive an ancillary device (not shown). In some examples, the axial movement of the ancillary device in the central channel (not shown), can be controlled by an external motorized sled to automatically deploy or retract the ancillary device with precision. In alternative examples, the ancillary device can be manually adjusted to control the insertion depth of the device in the central channel.

Exemplary Ancillary Devices and Uses of the Central Channel

The port 418 can receive a number of different ancillary devices, including but not limited to those shown in relation to FIGS. 7-10.

With particular reference to reversible and irreversible electroporation, an adaptive control of the pulsed electric field (PEF) treatment zone profile can be augmented with sensing technology that can be delivered through the central channel of the electrode assembly. The sensor can use signals like motion, sound, field, impedance or temperature for closed loop feedback. In various embodiments, the system includes an integrated control system to both isolate and time the PEF bursts with sensing capability which can use electrical fields, impedance, optical visualization, temperature, motion, sound, or other sensing modalities. Sensing can occur between pulses, between PEF bursts, or both.

A sensing probe, such as a probe with ultrasound, electrical, thermal or optical capabilities, can be timed for electric isolation from pulse generation in order to minimize distortion so that a controlled electrical isolation therapy is delivered. PEF therapy is delivered in a very low duty cycle with respect to video imaging, ultrasound or alternative sensing circuits. The control system can disconnect the sensing circuit while PEF cycles are delivered. The controlled imaging could be used in real time indications of effectiveness of treatment.

An impedance map can provide tissue electrical measurement. Combining an impedance map with known probe geometry can be used to generate a 3D model of the calculated treatment site. Alternatively, the therapy electrodes can also independently measure current through each tine via a multipath current sense on a multielectrode probe. This can be combined with voltage sense over the load to calculate the impedance of each electrode pair's individual path. The system can use impedance as an automated indicator of treatment efficacy.

Ultrasound Imaging Catheter

Figure 7:
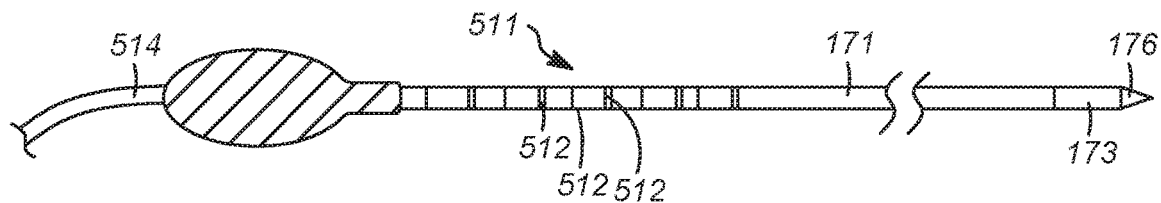
FIG. 7 is a side view of a biopsy needle according to some examples.

FIG. 7 is a side view of an ultrasound probe according to some examples. The ultrasound imaging catheter 171 includes an ultrasound transducer 173 configured to provide an ultrasound image of tissue. The ultrasound imaging catheter 171 may have a high speed rotational mechanism to create a two-dimensional image of the area around it. Commercially available options for ultrasound imaging catheters available from Boston Scientific Corporation, Inc. with offices in Marlborough, MA, USA include the OPTI-CROSS™ catheters. Intervascular ultrasound systems are described in the following patent documents filed by Boston Scientific Scimed, Inc., which are hereby incorporated herein by reference: U.S. Pat. Nos. 8,206,308; 8,257,267; 9,451,929; US20110071400; and US20120253197.

The distal tip 176 of the ultrasound catheter 171 can be introduced into the port 418 which opens into the central channel 141. The proximal portion 511 of the ultrasound catheter 171 can be provided with multiple evenly spaced depth markings 512 that allow a user to control the insertion depth of the catheter 171. A cable 514 provides an electrical connection between the ultrasound transducer 173 and the processor 404 of FIG. 6.

The ultrasound transducer 173 can be used to monitor the progress of ablation during an ablation procedure. For example, during the process of irreversible electroporation, in some cases tissue will show immediate edema injury following pulsed electric field energy delivery. These tissue changes are detectable by an ultrasound transducer. The ultrasound catheter 171 can be deployed into patient tissue at a first deployed position to collect a first ultrasound image of the tissue. The ultrasound catheter 171 can then be deployed into a second position by sliding the catheter 171 through the central channel 141. A second ultrasound image of the tissue can be collected at the second position. From these images, a three-dimensional (3D) image can be constructed, showing the condition of the tissue being ablated. Based on the feedback from the 3D ultrasound image, one or more therapy parameters can be adjusted. For example, the probe can be repositioned; the tines can be repositioned, retracted, or expanded; ablation can be resumed or halted; or a drug can be delivered into the tissue.

In some examples of the technology, the ultrasound transducer can be a 30 megahertz or 40 megahertz ultrasound sensor. The viewing radius of the ultrasound sensor can be about 1.5 centimeters (i.e., 3 cm in diameter) or beyond such as 3 cm (i.e., 6 cm in diameter). The viewing radius depends on the frequency, media (e.g., solid tissue vs. blood) and the power of the ultrasound sensor.

In some examples, the ultrasound probe can move all the way to the lesion outer diameter (e.g., 5 cm) to take initial images. Subsequent images can be taken as it retracts into the probe body, for example, every 0.5 cm. The combined images from all the locations can create a 3D visualization of the progress of the ablation. As an example, a lesion with a 5 centimeter diameter can be viewed using the ultrasound catheter by inserting the ultrasound sensor to the outer perimeter of the lesion and capturing an image at that location, then moving the ultrasound catheter a small distance (e.g., 2 cm) and taking a second image at the second location. The combined images from the two locations can create a 3D visualization of the progress of the ablation.

In some examples, the ultrasound imaging catheter has a diameter of at least 0.01 inches (0.25 mm). In some examples, the ultrasound imaging catheter has a diameter of 0.032 inches (0.81 mm) or less. In some examples, the ultrasound imaging catheter has a diameter of about 0.01 inches (0.25 mm) to 0.04 inches (1.02 mm), 0.015 inches (0.38 mm) to 0.032 inches (0.81 mm), or 0.017 inches (0.43 mm) to 0.026 inches (0.66 mm), inclusive of those values. In one example, a 30 megahertz (MHz) ultrasound imaging catheter can be introduced into a central channel having a diameter of about 0.0295 inch (0.75 mm), with a viewing distance of 1.5 cm, providing a viewing area 3 cm in diameter). In another example, a 40 megahertz (MHz) ultrasound imaging catheter, with an outer diameter smaller than the 30 MHz catheter, can fit in a central channel having a diameter of about 0.027 inch (0.69 mm).

Biopsy Needle

Figure 8:
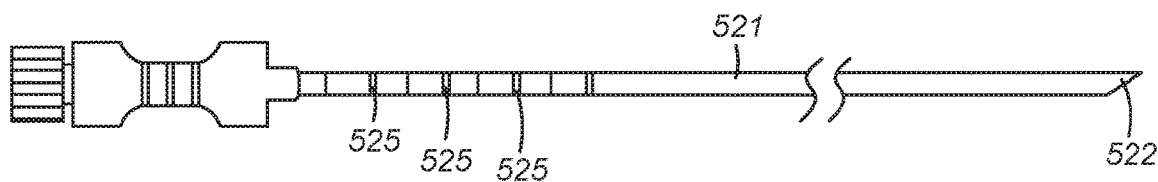
FIG. 8 is a side view of an ultrasound probe according to some examples.

FIG. 8 is a side view of a biopsy needle 521 that can be used as an ancillary device. The biopsy needle 521 has a sharp tip 522 for removing a tissue sample for biopsy. The biopsy needle 521 can include depth markings 525 that indicate the insertion depth of the device. In some examples, the biopsy needle 521 has a diameter of at least 25 Ga (0.51 mm). In some examples, the biopsy needle 521 has a diameter of 16 Ga (1.65 mm) or smaller. In some examples, the biopsy needle 521 has a diameter between 25 Ga and 16 Ga. In some examples, the biopsy needle can have a size of 19 Ga (1.07 mm), 22 Ga (0.72 mm), or 25 Ga (0.51 mm). Biopsy of tissue to be ablated can be performed before ablation, after ablation, or both before and after ablation.

Sensor Probe

Figure 9:
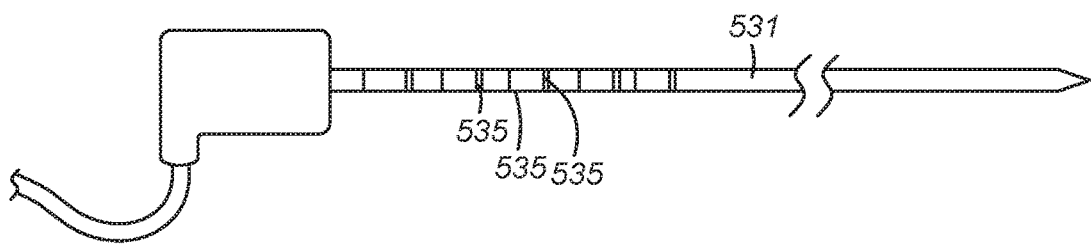
FIG. 9 is a side view of a sensor probe according to some examples.

FIG. 9 is a side view of a sensor probe 531 that can be used as an ancillary device in the system. In some examples the sensor probe 531 has depth markings 535 so that it can be positioned at locations of interest within patient tissue. The sensor probe 531 can be a temperature sensor, an impedance sensor, or other similar type of sensor. The sensor probe can include temperature sensing (thermocouple, thermistor, fiber optic sensors) and audible or pressure wave sensing (piezoelectric such as using lead zirconate titanate (PZT), accelerometer, audible cues, ultrasound, vibration). In some examples, the sensor probe 531 has a diameter of at least 0.01 inches (0.25 mm). In some examples, the sensor probe 531 has a diameter of 0.04 inches (1.02 mm) or less. In some examples, the sensor probe 531 has a diameter between about 0.01 inches (0.25 mm) and about 0.04 inches (1.02 mm). In some examples, the sensor probe 531 has a diameter of between 0.01 inches (0.25 mm) and 0.04 inches (1.02 mm), between 0.015 inches (0.38 mm) and 0.032 inches (0.81 mm), or between 0.017 inches (0.43 mm) and 0.026 inches (0.66 mm). Sensing of tissue can be performed before ablation, after ablation, or both before and after ablation. An optical or thermal camera can be used to evaluate the treatment site as well as determine effectiveness of the ablation treatment.

The position of the sensor probe is adjustable so it can be positioned by the physician to locations of interest, for example a feeding artery or a diaphragm. During radiofrequency ablation, a temperature reading can be used to ensure the local temperature is high enough to kill the tumor tissue or low enough to avoid unwanted damage to non-diseased tissue. In one example, the sensor can be a thermocouple using bare T-type thermocouple wires with a single wire diameter of 0.003 inch (0.076 mm) and an outer diameter of 0.006 inch (0.15 mm) diameter.

Fluid Delivery Device

Figure 10:
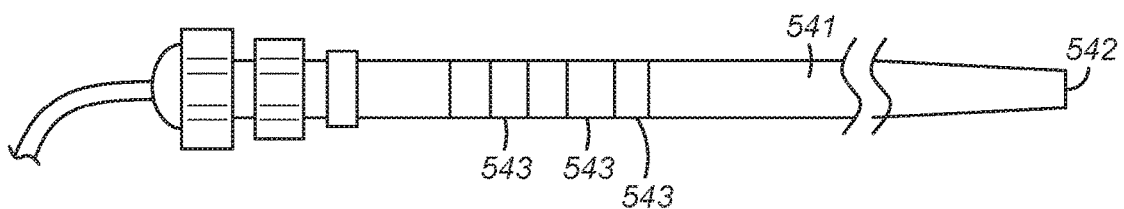
FIG. 10 is a side view of a drug delivery device according to some examples.

FIG. 10 is a fluid delivery device 541 that can be used as an ancillary device in the system. Liquid can be injected into the tissue through the distal tip 542 of the fluid delivery device 541 to adjust local tissue electrical conductivity. Saline can be used to increase the conductivity and glucose can be used to decrease the conductivity. In some examples of radiofrequency ablation, a saline injection is used to form a virtual electrode. In some examples of pulsed electric field therapy, saline or glucose can be used to manipulate the electric field. In some examples, the device 541 includes depth markings 543.

Other Exemplary Uses of the Central Channel

Additional uses of the central channel 141 are contemplated. For example, local drug delivery can be administered through the central channel 141. Examples of drugs that can be delivered include chemotherapy drugs, immunotherapy drugs, other biologic molecules, and alcohols for chemical ablation.

Delivery of Other Substances During Electroporation Using the Central Channel

The electric field distribution of applied irreversible electroporation treatments can be affected by substituting the permeable liquid with a material of either higher electrical conductivity in tissue, such as electrical conductivity of greater than 0.1 Siemens per meter (S/m) or lower conductivity fluids in blood vessels, such as electrical conductivity of less than 0.1 S/m) to reduce the conductivity sink from major blood vessels, such that the maximum volume covered by sublethal field magnitudes can be greater and increase the coverage of lethal irreversible electroporation and sublethal reversible electroporation treatment regions. Infusion of isotonic conductivity liquids into nearby tissue could improve the volume of treatment. After pulsed electric field treatment, a mechanism to deliver healthy cells to the cancerous site can also be completed with an infusion through the central channel to expedite new healthy cell growth.

In some examples, the electrode assembly is configured for fluid delivery through the central channel, such as when a syringe is used to inject fluid through a port external to the ablation catheter and into the central channel. A conductive or tissue-permeating fluid can be introduced in order to promote a targeted electrolyte delivery with an ionic solution. A conductive polymer can be introduced to enable electric field propagation into tissue and to improve the penetration or distribution uniformity of an applied electric field, effectively increasing the application size of the electrodes. Introduction of either a conductive or semi-permeable media prior to or during electroporation energy delivery can alter the propagation of the electric field to enable more homogeneous tissue distribution of the electrical energy across varying tissue heterogeneity that may otherwise impede, absorb, or misdirect the electric field range affecting the ablation depth of the ablative pulses applied. Various device designs provide a dual action of ablation and treatment with a compound. The ablation can treat the surface of tissue or cellular material that has a hyperplastic or cancerous indication. The electroporation provides a therapeutic window for delivery of a cytotoxic compound with a permeable, rapid, or sustained release.

Various conductivity enhancements in the form of a diffused solution can be introduced as a bolus injection or through a permeable membrane, such as a balloon catheter. Alternatively or in addition, enhancements can be made to affect cellular membranes or gross tissue for electrical field propagation via the cells' transmembrane potential. In addition, conductive vessels, either fast releasing agents or as a biodegradable polymer sac holding a conductive solution can be designed for controlled fluid release. The conductive fluid, alone or in combination with a cytotoxic drug loaded with a chemotherapeutic or immunotherapeutic material, can help facilitate local tissue treatment at the ablation zone. The irreversible electroporation electrode could be embodied as a monopolar electrode element, delivering a bolus of conductive solution, with an external grounding pad to facilitate larger virtual electrode with resulting treatment volume. Electrochemotherapy drug delivery could be accomplished via various catheter designs, for example, irrigated tines, needles or catheter shafts, porous or electrospun balloon, the central channel in the ablation catheter, or via a part of the catheter system that is left behind in the patient's body.

As one example, the central channel can be used to introduce benign, non-toxic, isotonic or polyelectrolytic solutions during pulsed electric field treatments. These substances can provide a higher localized tissue or paracellular conductivity to aid in the electric field threshold upon activation of a pulsed electric fields (PEF). An ion-rich media of opposite polarity can also provide intent to prime field of cells. A 2× (or 1× for mono-polar) high pressure bolus injections of conductive media such a saline can create virtual electrodes within tissue by creating conductive surface areas in tissue; this can be used with bipolar ablation. An intentional polarization or "charging" of tumor tissue enhances the polarized and targeted homing via electrophoresis and iontophoresis.

Additionally, during irreversible electroporation therapy, electrically charged cationic polymers or biomaterials, such as synthetic polymethacrylate (PAHM) or calcium carbonate, can be delivered to the cell surface, which in the presence of a pulsed electric field will cause cell membrane instability and lower the field thresholds necessary to permeate and irreversibly disrupt the cell bilipid layer.

The central channel can also be used to deliver chemotherapy solutions for dose dependent targeted concentrations, or chemotherapeutic agents mixed with various isotonic solutions such as saline or pH buffered materials to increase local tissue conductivity in the presence of pulsed electric fields.

The central channel can also be used to deliver immunotherapy materials including monoclonal antibodies, checkpoint inhibitors, biomaterials such as protein, peptides, long-chain cationic polymer materials or other cytotoxic agents for localized delivery in the presence of pulsed electric fields. Additionally, radiopaque slurry mixtures either with known contrast agents or loaded microparticles or spheres to improve local visualization (e.g. fluoroscopy or ultrasound) can be introduced via the central channel.

The central channel can also be used to deliver biostable or biodegradable materials in the form of foams, gels, or micro-embolic particles that can either be absorbed through hydrolytic degradation or other disintegration mechanisms. Alternatively, permanent implantable materials that are porous or semi-porous with a coating shell or lining material that degrades over time can be introduced. The degradation rate of the biodegradable materials allow a slow release of a drug or a biocompatible mixture of drugs to provide localized and sustained drug release.

The central channel can also be used to deliver magnetic or radiation-absorbing nanoparticles that can demonstrate hyperthermic heating either mixed with a cytotoxic agent or other drug-loaded mixture.

The central channel can also be used to deliver liposome or exosome materials that are constructed with a multiple constituent design that allows monoclonal antibodies or other chemo or immunoncology agents to be delivered without compromising its morphology or biological activity once implanted on the cell surface or with the intracellular fluid to target the nucleus or cell division process (mitosis).

Control of Axial Movement of Ancillary Device

Ancillary devices can be inserted, retracted, and moved within the central channel by a number of different methods. Control can be manual, for example when an ancillary device is inserted by hand into a port. In this situation, the ancillary device can have multiple insertion depth markings on the shaft in the ancillary device. The markings can be evenly spaced and labeled to indicate the insertion depth of the ancillary device. Alternatively or in addition, the system can provide a locking mechanism that holds the ancillary device in place with respect to the ablation catheter. Alternatively or in addition, the ancillary device can be provided with mechanical means to move the device within the central channel, such as a screw assembly that translates rotational motion of a screw to linear axial motion of the ancillary device. Alternatively or in addition, insertion and retraction of the ancillary device can be controlled electronically using a motored assembly.

Shaft of Elongate Electrode Assembly

In some examples, the structure that defines the central channel can be a solid tube made of a suitable material. In some examples, the shaft of the elongate electrode assembly includes a coiled material or micromachined material. Suitable materials include stainless steel or a polymer. In some examples, a lining can be provided on the inner diameter of the tube. If drugs are to be injected through the central channel, for example, the lining can be provided to protect sensitive drugs from interacting with the material of the tube. The tube can be provided with a compression tensile sufficient to deploy and retract the tube within the ablation catheter in response to a linear force on the proximal end of the tube. In some examples, the tube has a wall thickness of between about 0.003 inches (0.08 mm) and 0.05 inches (1.27 mm). In some examples, the tube has a wall thickness of between about 0.005 inches (0.13 mm) and 0.01 inches (0.25 mm). In some examples, the tube has an inner diameter of between about 0.01 inches (25 Ga, 0.25 mm) and 0.106 inches (12 Ga, 2.69 mm). In some examples, the tube has an inner diameter of between about 0.016 inches (22 Ga, 0.41 mm) and 0.063 inches (14 Ga, 1.6 mm), or between about 0.024 inches (20 Ga, 0.61 mm) and 0.042 inches (17 Ga, 1.07 mm). In some examples, the tube has an outer diameter of between about 0.02 inches (25 Ga, 0.51 mm) and 0.134 inches (10 Ga, 3.40 mm), between about 0.028 inches (22 Ga, 0.71 mm) and 0.083 inches (14 Ga, 2.11 mm), or between about 0.036 inches (20 Ga, 0.91 mm) to 0.058 inches (17 Ga, 1.47 mm). In some examples, the tube has a length of between about 5 cm and 40 cm, between about 10 cm and 25 cm, or between about 15 cm and 20 cm. In one example, the tube is an Society of Automotive Engineers (SAE) type 304 stainless steel tube with an inner diameter of 0.027 inch (0.69 mm), an outer diameter of 0.039 inch (0.99 mm), and a wall thickness of 0.006 inch (0.15 mm).

Leads

The electrode assemblies of the various examples of the technology are provided with electrically conductive leads to convey energy from a generator outside of the ablation catheter to the electrodes inside of a patient's body. The leads are configured to electrically connect the electrode elements of the electrode assembly to an external generator. The leads can be situated in a number of different configurations, based on the particular implementation of the ablation catheter. For example, the body of the electrode assembly itself can be constructed from an electrically conductive material, such as stainless steel, in which case the body can serve as the lead. In alternative examples, a wire positioned on the inner surface or the outer surface of the electrode assembly shaft can be used as a lead. In alternative examples, a lead can be placed within the wall of the electrode assembly, or the lead can be a conductive trace on the inner surface or the outer surface of the electrode assembly.

Each electrode assembly is provided with at least one lead. A separate lead can be provided for each electrode of an electrode assembly, so that individual electrodes can be held at different potentials.

Electrode Elements and Electrode Arrays

While particular exemplary embodiments of electrode elements and electrode arrays are provided, the disclosure is not limited to the specific examples herein. Additional configurations are contemplated. In some examples, the electrode arrays are expandable from a first retracted position inside of the ablation catheter to an expanded position outside of the ablation catheter. In some examples, the electrode array comprises two or more electrode elements positioned at the distal portion of the electrode assembly. In some examples, the electrode array comprises three or more electrode elements positioned at the distal portion of the electrode assembly. The electrode array can be configured so that when the electrode elements are expanded and deployed, the electrode elements surround the exterior of the ablation catheter circumferentially, although this is not necessary. In some examples, the electrode elements can be deployed selectively such that some electrode elements are in a retracted position at the same time that other electrode elements are in an expanded position. In some examples, multiple electrode elements are present and the distance between the electrode elements is adjustable.

In some examples, the electrode elements can be electrically conductive tines, such as a conductive shape memory alloy material such as nickel titanium alloy (nitinol). In alternative examples, the electrode elements can be stainless steel, gold plated stainless steel, platinum, or other conductive metals or alloys.

The electrode elements of the various examples can be attached to the electrode assembly using a number of different constructions. For example, if the electrode assembly shaft is metal and the electrode elements are metal, the two can be welded together. In alternative arrangements, the electrode elements can be integrally constructed from the electrode assembly material, such as one when the electrode assembly shaft is a metal tube. In this example, the tube can be cut to the correct proportions to create the electrode elements. In alternative examples, the electrode elements can be attached using a collar or could be looped through openings at the end of the shaft.

Ablation Methods

The various examples of ablation catheter as provided herein can be used to implement an ablation method. The method uses an ablation probe including a sheath, an electrode assembly with a central channel, and one or more ancillary devices. The sheath is provided with a sheath lumen in which the electrode assembly can be situated. The ancillary device is insertable into the central channel of the electrode assembly. The method includes the step of inserting the sheath into tissue of the patient. This step can include, for example, percutaneous insertion of the sheath into patient tissue through the skin. Other insertion methods are possible and are within the scope of the present technology.

The method further includes inserting the electrode assembly into the sheath lumen. This step can be performed before or after insertion of the sheath into the patient tissue. While the electrode assembly is inside of the sheath lumen, patient tissue is ablated using the electrode assembly. Some examples of the technology include the step of expanding electrode elements of the electrode assembly into the patient tissue after the step of inserting the electrode assembly into the sheath lumen, and ablating the tissue after the electrode elements have been expanded.

The method further includes the step of inserting the ancillary device into the central channel of the electrode assembly. In some examples, the step is performed while the electrode assembly is inside of the sheath lumen and optionally while the sheath is inside of patient tissue.

Some examples of the technology include, after the step of ablating the tissue, while the ancillary device is inside of the electrode assembly, using the ancillary device to capture an image of the patient tissue, sense a condition of the patient tissue, deliver a fluid into the patient tissue, or remove at least a portion of the patient tissue through the central channel. An image can be captured using an ultrasound imaging catheter or an optical or thermal camera. Sensing a condition of the patient tissue can include sensing temperature, impedance, or other qualities of the patient tissue using a sensor probe. Delivering a fluid into the patient tissue can include delivering a medical fluid such as a pharmaceutical drug, chemotherapy, or other medical fluids through a catheter or needle.

In one example of the disclosed technology, the ancillary device is an ultrasound imaging catheter. The method includes the step of inserting the sheath into tissue of a patient, inserting the electrode assembly into the sheath lumen, and while the electrode assembly is inside of the sheath lumen, performing reversible or irreversible electroporation of the tissue using the electrode assembly using pulsed electric field energy. The method further includes while the electrode assembly is inside of the sheath lumen, inserting the ultrasound imaging catheter into a proximal portion of the central channel of the electrode assembly and out distal end of the central channel such that the ultrasound imaging catheter protrudes from the distal end of the electrode assembly. The method further includes capturing an ultrasound image of the patient tissue while the ultrasound imaging catheter protrudes from the distal end of the electrode assembly.

In some examples, capturing the ultrasound image includes capturing the ultrasound image when the ultrasound imaging catheter is protruding from the distal end of the electrode assembly a first distance in a first location of patient tissue. The method further includes moving the ultrasound imaging catheter to a second position in the patient tissue such that the ultrasound imaging catheter is protruding from the distal end of the electrode assembly a second distance, and capturing a second ultrasound image. The ultrasound images are captured using an ultrasound transducer at the distal tip of the ultrasound imaging catheter. Electrical signals from the ultrasound transducer are transmitted to an external processor. In some examples, the ultrasound images are combined to provide a 3D ultrasound image of the patient tissue. The 3D ultrasound image is capable of showing a change in patient tissue caused by the ablation.

In some examples, the method further includes using the captured ultrasound image to determine that additional ablation of the tissue is required. In some examples, the method includes the step of further ablating the tissue using the electrode assembly after capturing the ultrasound image.

In alternative examples of the technology, the method includes inserting the sheath into tissue of the patient, inserting the electrode assembly into the sheath lumen, and delivering a fluid into patient tissue through the central channel. For example, a fluid such as saline or glucose can be inserted into tissue through the central channel. Alternatively, pharmaceuticals, drugs, cells, chemicals, genes, proteins, viruses, or embolics can be introduced through the central channel into patient tissue. In some examples, a syringe external to the system interlocks with a port in communication with the central channel, and fluid is transmitted from the syringe through the central channel to the patient tissue.

Parameters for Radiofrequency Ablation

In various examples, such as using the radially expandable member of FIG. 4, the energy has a frequency about 20 kHz to 5 MHz, or about 400 kHz to 500 kHz, for example 460 kHz. The target temperature for the embedded temperature sensor is about 60° C. to 95° C., or about 80° C. The duration of radiofrequency energy application ranges from about 10 seconds to 5 minutes, or ranges from about 30 seconds to 2 minutes.

The energy can be applied (1) simultaneously, (2) sequentially or (3) in a time switching manner. A time switching manner means the energy is applied to one or more selected electrodes for a short period, such as 20 milliseconds, and then energy is applied to one or more other selected electrodes for another short period. The energy application switches quickly among electrodes.

Parameters for Irreversible Electroporation

For irreversible electroporation, which is one type of PEF therapy, the pulse width ranges from 10 nanoseconds to 1 millisecond, or 1 microsecond to 75 microseconds. The pulse can be either biphasic, having both positive and negative phases, or monophasic. The voltage ranges from 200 V to 5000 V, or 1000 V to 3000 V, to have the electrical field strength in tissue from 500 V/cm to 2000 V/cm, such as 1000 V/cm to 1500 V/cm to cause cell damage.

Parameters for Electroporation to Facilitate Drug Penetration

For reversible electroporation, which is one type of PEF therapy, the pulse width ranges from 10 nanoseconds to 1 milliseconds, preferably 1 microsecond to 75 microsecond. The pulse can be either biphasic, having both positive and negative phases, or monophasic. The voltage ranges from 50 V to 5000 V, such as 100 V to 3000 V, to have the electrical field strength in tissue from 50 V/cm to 800 V/cm, such as 100 V/cm to 400 V/cm, to cause reversible cell damage to allow drug to penetrate the membrane.

As used in this specification and the appended claims, the singular forms include the plural unless the context clearly dictates otherwise. The term "or" is generally employed in the sense of "and/or" unless the content clearly dictates otherwise. The phrase "configured" describes a system, apparatus, or other structure that is constructed or configured to perform a particular task or adopt a particular configuration. The term "configured" can be used interchangeably with other similar terms such as arranged, constructed, manufactured, and the like.

All publications and patent applications referenced in this specification are herein incorporated by reference for all purposes.

While examples of the technology described herein are susceptible to various modifications and alternative forms, specifics thereof have been shown by way of example and drawings. It should be understood, however, that the scope herein is not limited to the particular examples described. On the contrary, the intention is to cover modifications, equivalents, and alternatives falling within the spirit and scope herein.

The invention claimed is:

1. A system for ablation comprising:
   a catheter comprising:
      a sheath defining a sheath lumen and a distal end,
      an elongate electrode assembly within the sheath lumen, the electrode assembly having a distal portion and a proximal portion, the electrode assembly being axially moveable within the sheath lumen, the electrode assembly comprising:
         a shaft defining a central channel and a distal central channel opening,
         a first lead within the shaft, and
         an expandable electrode array comprising two or more electrode elements positioned at the distal portion of the electrode assembly and electrically connected to the first lead, wherein the electrode array is moveable between a retracted position contained within the sheath lumen and an expanded position protruding from the sheath, wherein the electrode elements surround the distal central channel opening of the shaft when the electrode elements are in the expanded position, wherein the two or more electrode elements include free distal ends and proximal ends attached to an inner surface of the shaft;
   a handle assembly operably connected to the electrode assembly, the handle assembly comprising a port;
   an ultrasound imaging catheter configured to be slidably moved within the central channel, wherein the ultrasound imaging catheter is capable of being moved axially between a first deployed position and a second deployed position, wherein the ultrasound imaging catheter extends away from the distal central channel opening by a first distance in the first deployed position and by a different second distance in the second deployed position;
   a liquid delivery device configured to be introduced into and slidably moved within the central channel while the ultrasound imaging catheter is positioned within the central channel; and
   a computer processor in communication with the ultrasound imaging catheter, wherein the processor is configured to generate a first ultrasound image of tissue when the ultrasound imaging catheter is in the first deployed position, and further configured to generate a second ultrasound image when the ultrasound imaging catheter is in the second deployed position.

2. The system of claim 1 wherein the electrode elements protrude from the distal end of the sheath in the expanded position.

3. The system of claim 2 wherein the electrode elements comprise electrode tines, wherein the electrode tines are moved to the expanded position when a linear force is applied to the electrode assembly within the sheath lumen so that electrode assembly protrudes from the distal end of the sheath.

4. The system of claim 3 wherein a position of the electrode tines in the expanded position is adjustable by adjusting an amount of protrusion of the electrode tines from the distal end of the sheath.

5. The system of claim 1 wherein the first lead is positioned on the inner surface.

6. The system of claim 1 wherein the shaft is a tube comprising a solid wall.

7. The system of claim 1, further comprising an ancillary device, wherein the ancillary device comprises a sensor and wherein the system further comprises a processor in communication with the sensor, wherein the processor is configured to generate at least one of the group consisting of a signal corresponding to an impedance of tissue to detect a change in tissue due to ablation and a signal corresponding to a temperature of tissue to detect a change in tissue due to ablation.

8. The system of claim 1 wherein the electrode assembly is configured for fluid delivery through the central channel.

9. The system of claim 1 further comprising a generator configured to be electrically connected to the electrode assembly and for delivery of one of the group consisting of a radiofrequency energy, a pulsed electric field, an irreversible electroporation energy, and a reversible electroporation energy.

10. A system for ablation comprising:
   a catheter comprising:
      a sheath defining a sheath lumen and a distal end, an elongate electrode assembly within the sheath lumen, the electrode assembly having a distal portion and a proximal portion, the electrode assembly being axially moveable within the sheath lumen, the electrode assembly comprising:
         a shaft defining a central channel and a distal central channel opening, a first lead within the shaft, and
         an expandable electrode array comprising three or more electrode elements positioned positioned at the distal portion of the electrode assembly and electrically connected to the first lead, wherein the electrode array is moveable between a retracted position contained within the sheath lumen and an expanded position protruding from the distal end of the sheath, wherein the electrode elements surround the distal central channel opening of the shaft when the electrode elements are in the expanded position, wherein the three or more electrode elements include free distal ends and proximal ends attached to an inner surface of the shaft;
   an ultrasound imaging catheter configured to be slidably moved within the central channel, wherein the ultrasound imaging catheter is capable of being moved axially to a first deployed position extending from the distal central channel opening;
   an ancillary delivery device configured to be introduced into and slidably moved within the central channel while the ultrasound imaging catheter is positioned within the central channel; and a generator configured to be electrically connected to the electrode assembly and configured for delivery of one of the group consisting of a radiofrequency energy, a pulsed electric field, an irreversible electroporation energy, and a reversible electroporation energy.

11. The system of claim 10 wherein the electrode elements comprise electrode tines, wherein the electrode tines are moved to the expanded position when a linear force is applied to the electrode assembly within the sheath lumen so that the electrode assembly protrudes from the distal end of the sheath.

12. An ablation method comprising:

providing an ablation probe system having:

a sheath having a sheath lumen, an electrode assembly defining a central channel, the electrode assembly further comprising a shaft and an expandable electrode array comprising two or more electrode elements positioned at a distal portion of the shaft, wherein the shaft is moveable between a retracted position contained within the sheath lumen and an expanded position with the electrode array protruding from the sheath, wherein the electrode elements surround a distal central channel opening when the electrode elements are in the expanded position, wherein the two or more electrode elements include free distal ends and proximal ends attached to an inner surface of the shaft, an ultrasound imaging catheter configured to be inserted in the central channel, a liquid delivery device configured to be introduced into and slidably moved within the central channel while the ultrasound imaging catheter is positioned within the central channel;

inserting the sheath into tissue of a patient;

inserting the electrode assembly into the sheath lumen;

while the electrode assembly is inside of the sheath lumen, ablating the tissue using the electrode assembly;

while the electrode assembly is inside of the sheath lumen, inserting the ultrasound imaging catheter into a proximal end of the central channel and out a distal end of the central channel such that the ultrasound imaging catheter protrudes from a distal portion of the electrode assembly; and capturing an ultrasound image of the tissue while the ultrasound imaging catheter protrudes from the distal portion of the electrode assembly and further while the tissue is ablated.

13. The ablation method of claim 12, the method further comprising:

after the step of inserting the electrode assembly into the sheath lumen, expanding the electrode elements into the patient tissue; and performing the step of ablating the tissue after the electrode elements have been expanded.

14. The ablation method of claim 12, the ablation probe system further comprising an ancillary device, the method further comprising while the ancillary device is inside of the electrode assembly, using the ancillary device to perform at least one of:

sensing a condition of the patient tissue;

delivering a fluid into the patient tissue; or removing at least a portion of the patient tissue through the central channel.

* * * * *